(12) United States Patent
Satou et al.

(10) Patent No.: US 10,011,676 B2
(45) Date of Patent: *Jul. 3, 2018

(54) COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

(71) Applicant: DIC Corporation, Tokyo (JP)

(72) Inventors: Yutaka Satou, Ichihara (JP); Ayumi Takahashi, Ichihara (JP)

(73) Assignee: DIC Corporation, Tokyo (JP)

( * ) Notice: Subject to any disclaimer, the term of this patent is extended or adjusted under 35 U.S.C. 154(b) by 242 days.

This patent is subject to a terminal disclaimer.

(21) Appl. No.: 14/897,850

(22) PCT Filed: Feb. 21, 2014

(86) PCT No.: PCT/JP2014/054141
§ 371 (c)(1),
(2) Date: Dec. 11, 2015

(87) PCT Pub. No.: WO2014/199662
PCT Pub. Date: Dec. 18, 2014

(65) Prior Publication Data
US 2016/0137770 A1    May 19, 2016

(30) Foreign Application Priority Data

Jun. 14, 2013 (JP) ................. 2013-125565

(51) Int. Cl.
*C08G 8/02* (2006.01)
*C07C 39/15* (2006.01)
(Continued)

(52) U.S. Cl.
CPC ............... *C08G 8/02* (2013.01); *C07C 39/15* (2013.01); *C08G 59/621* (2013.01); *C08G 61/02* (2013.01);
(Continued)

(58) Field of Classification Search
CPC .................................................. C08G 8/02428
(Continued)

(56) References Cited

U.S. PATENT DOCUMENTS 7,985,822 B2    7/2011    Ogura et al.
8,263,714 B2    9/2012    Ogura et al.

FOREIGN PATENT DOCUMENTS

JP    41-012230 B    7/1966
JP    04-360146 A    12/1992
(Continued)

OTHER PUBLICATIONS

M. Victoria Gomez et al., "Synergy between microwave irradiation and heterogeneous catalysis in an environmentally friendly self-condensation of hydroxybenzene derivatives," ARKIVOC, 2010, (iii), pp. 264-273.
(Continued)

*Primary Examiner* — Duc Truong
(74) *Attorney, Agent, or Firm* — Locke Lord LLP

(57) ABSTRACT

There are provided a compound containing a phenolic hydroxyl group, which exhibits excellent heat resistance and excellent flame retardancy in terms of a cured product thereof, a phenolic resin including the same, a curable composition and a cured product thereof, a semiconductor sealing material, and a printed circuit board. The compound containing a phenolic hydroxyl group has a molecular structure represented by the following General Formula (I):

(Continued)

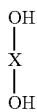

(I)

wherein X is a structural site represented by the following Structural Formula (x1) or (x2);

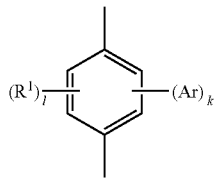

(x1)

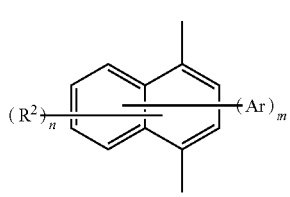

(x2)

in Formula (x1) or (x2), k is an integer of 1 to 3, m is 1 or 2, Ar is a structural site represented by the following Structural Formula (Ar1), and in a case where when k or m is 2 or greater, a plurality of Ar's may be the same as or different from each other;

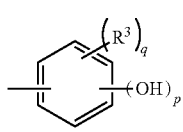

(Ar1)

wherein p is 1 or 2.

5 Claims, 4 Drawing Sheets

(51) Int. Cl.
C08G 61/02 (2006.01)
C08L 61/16 (2006.01)
H05K 1/03 (2006.01)
H05K 1/09 (2006.01)
C08G 59/62 (2006.01)
C07C 39/14 (2006.01)
H01L 23/29 (2006.01)
C08L 65/00 (2006.01)

(52) U.S. Cl.
CPC ............ *C08L 61/16* (2013.01); *H05K 1/0373* (2013.01); *H05K 1/09* (2013.01); *C08L 65/00* (2013.01); *H01L 23/295* (2013.01); *H01L 2924/0002* (2013.01)

(58) Field of Classification Search
USPC ......................................................... 428/457
See application file for complete search history.

(56) References Cited

FOREIGN PATENT DOCUMENTS

| JP | 06-049196 A | 2/1994 |
| JP | 2002-114889 A | 4/2002 |
| JP | 2013-023613 A | 2/2013 |
| JP | 5682804 B1 | 3/2015 |
| TW | 201305236 A | 2/2013 |

OTHER PUBLICATIONS

Ke-Qing Ling et al., "Copper(II)-Mediated Autoxidation of tert-Butylresorcinols," J. Org. Chem., 2003, 68(4), pp. 1358-1366.
Lee, In-Kyoung et al., "p-Terphenyls from Fungus *Paxillus curtisii* Chelate Irons: A Proposed Role of p-Terphenyls in Fungus," Journal of Microbiology and Biotechnology, First published online Mar. 12, 2013, 23(5), pp. 652-655.
A. J. Birch et al., "Studies in Relation to Biosynthesis, XXXIX. Oosporein," Australian Journal of Chemistry, 1969, 22(6), pp. 1319-1320.
G. Lloyd et al., "The Chemistry of fungi. Part XXV. *Oosporein, a Metabolite* of Chaetomium aureum *Chivers.*," Journal of the Chemical Society, 1955, pp. 2163-2165.
Hans-Erick Hogberg, "Cyclo-oligomerization of Quinones, V. The Acid Catalyzed Reactions of $_\alpha$-Naphthoquinone with Phenols", Acta Chemica Scandinavica, 1973, 27(7), pp. 2559-2566.
Rudolf Pummerer et al., "Die Kondensation von Chinonen mit Phenolen.", 3. Mitteilung uber Diarylchinone., Berichte der Deutschen Chemischen Gesellschaft [Abteilung] B: Abhandlungen, 1927, 60B, pp. 1442-1451.
International Search Report dated May 20, 2014, issued for PCT/JP2014/054141.
Office Action dated May 24, 2017, issued for the Taiwanese patent application No. 103110026.

[Fig.1]
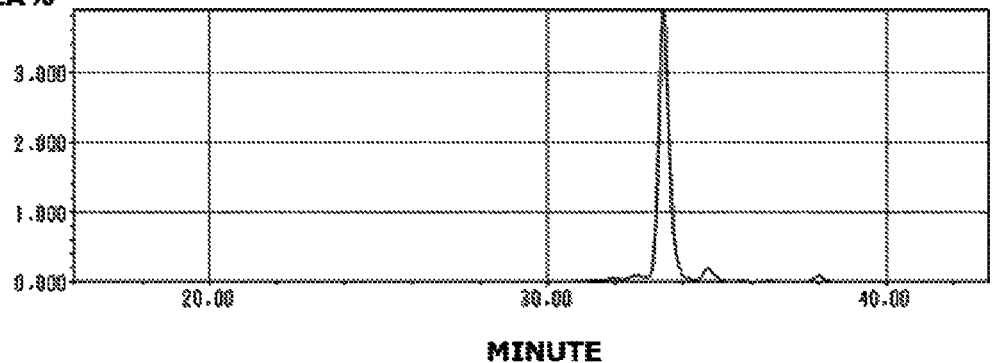
[Fig.2]
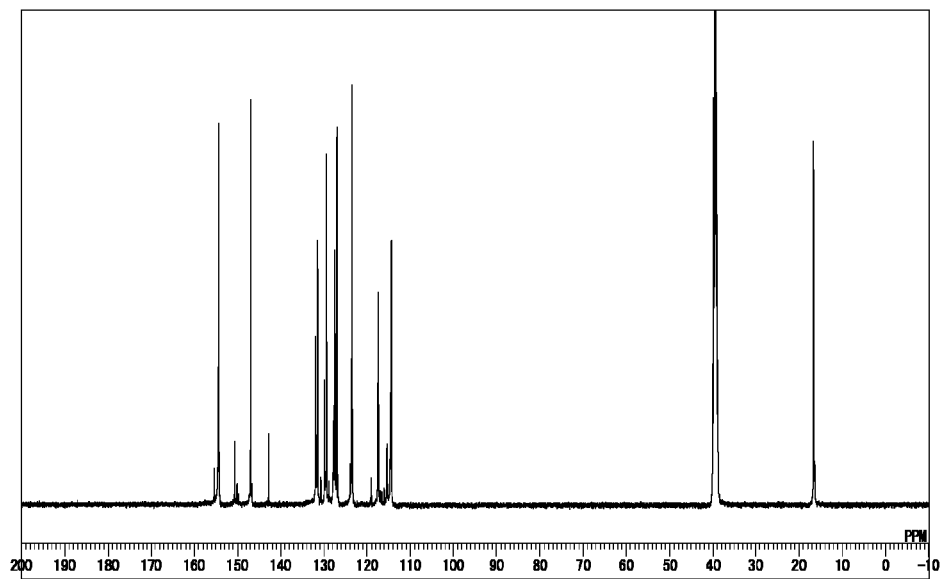

[Fig.3]
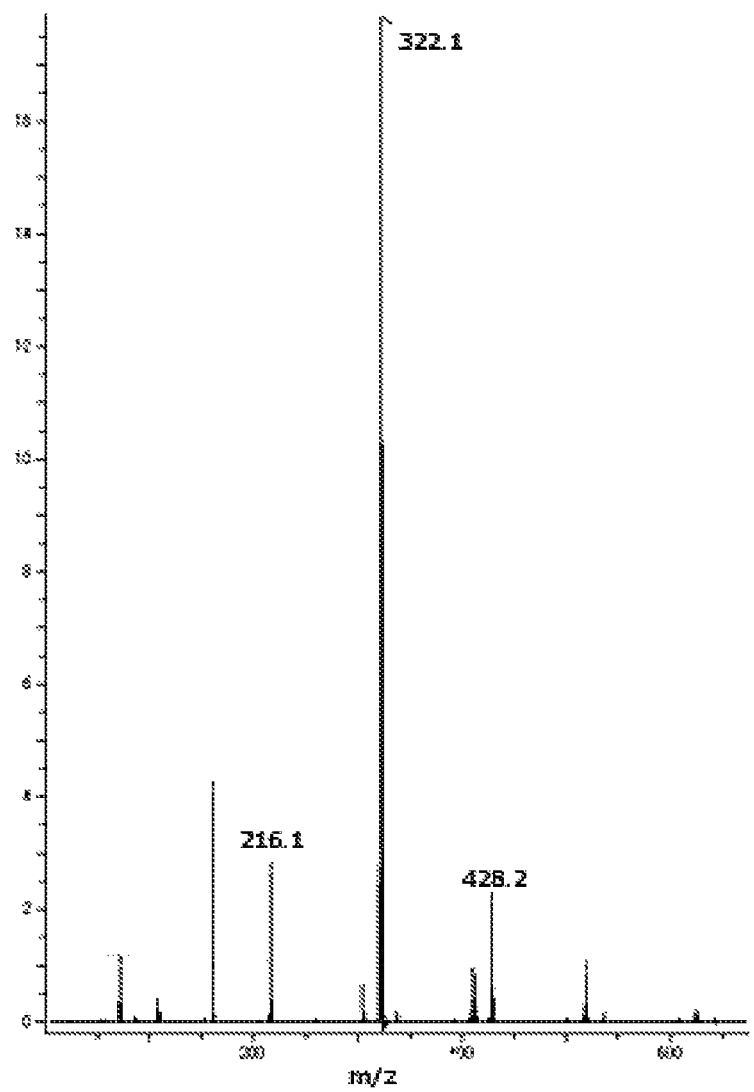

[Fig.4]
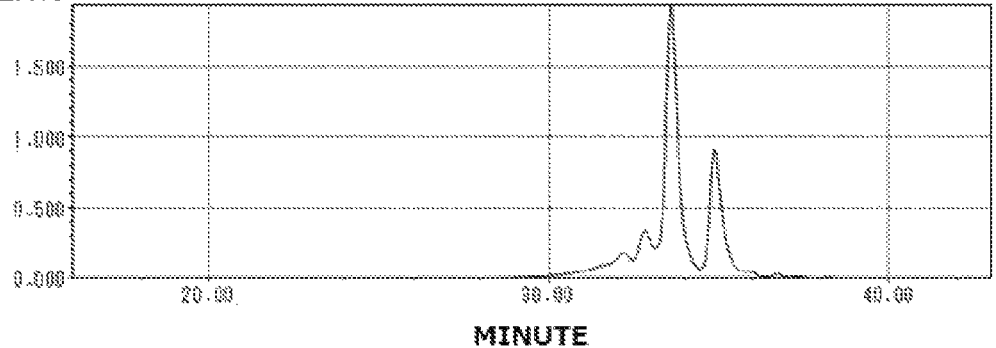
[Fig.5]
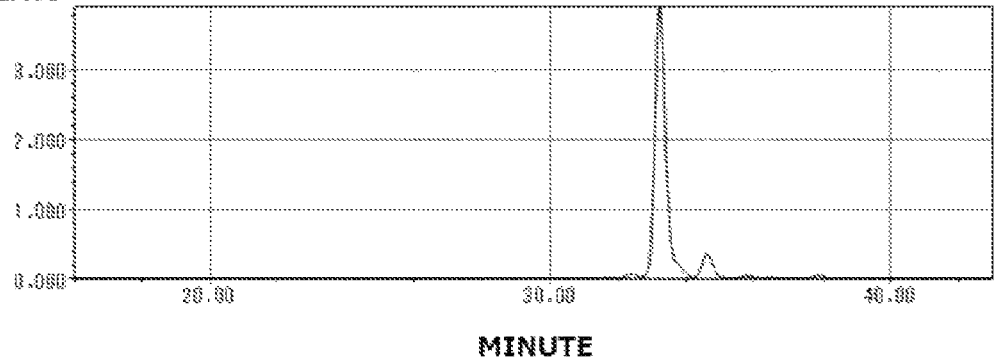

[Fig.6]
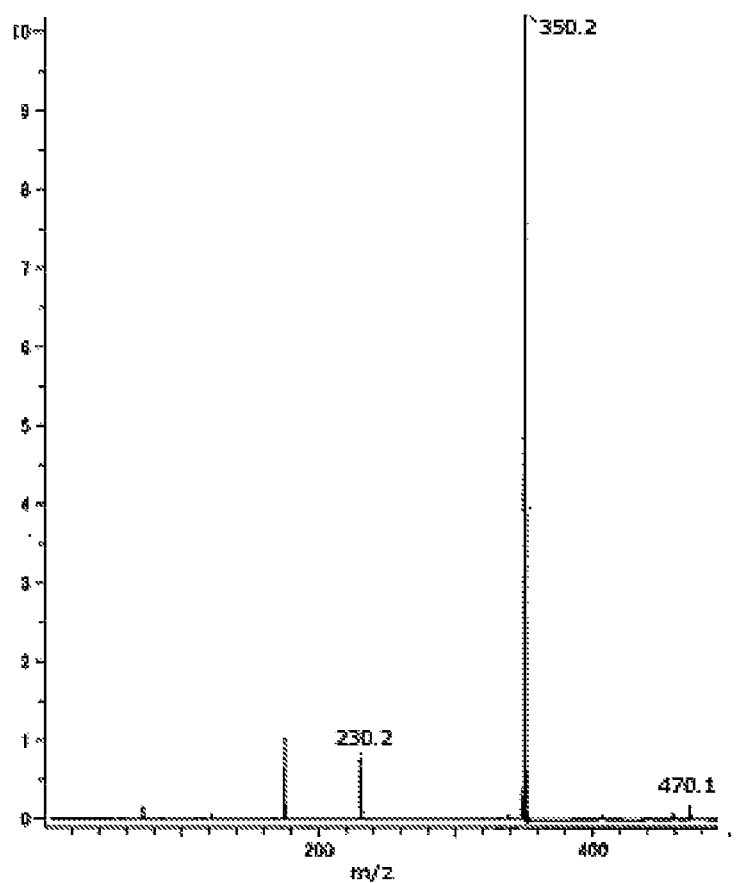

COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

CROSS REFERENCE TO RELATED APPLICATIONS

This application is related to co-pending application: "COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD" filed even date herewith in the names of Yutaka Satou and Ayumi Takahashi as a national phase entry of PCT/JP2014/054137, which application is assigned to the assignee of the present application and is incorporated by reference herein.

TECHNICAL FIELD

The present invention relates to a compound containing a phenolic hydroxyl group which exhibits excellent heat resistance and flame retardancy in terms of a cured product thereof, a phenolic resin including the same, a curable composition and a cured product thereof, a semiconductor sealing material, and a printed circuit board.

BACKGROUND ART

A phenolic resin has been used, for example, as a curing agent for epoxy resins, and an epoxy resin composition which is cured by a phenolic resin as a curing agent is widely used in electrical and electronic fields such as a semiconductor sealing material and a printed circuit board insulating material from the viewpoint that the cured product has excellent heat resistance and moisture resistance, in addition to an adhesive, a molding material, and a coating material.

Among these, a power semiconductor represented by a power module for an automobile is a technology crucial to energy saving in electrical and electronic equipment, and with a larger current, miniaturization, and high efficiency of a power semiconductor, transition from a silicon (Si) semiconductor in the related art to a silicon carbide (SiC) semiconductor has been advancing. The advantage of the SiC semiconductor is that the SiC semiconductor can be operated under higher temperature conditions, and therefore, a semiconductor sealing material is required to have higher heat resistance than those of semiconductor sealing materials in the related art. In addition, it is also important for the required performance of a semiconductor sealing resin to exhibit high flame retardancy without using a halogen-based flame retardant, and a resin material which has such performance has been required.

As the resin material to cope with these various required characteristics, for example, the compound containing a phenolic hydroxyl group represented by the following structural formula is known (refer to PTL 1).

[Chem. 1]

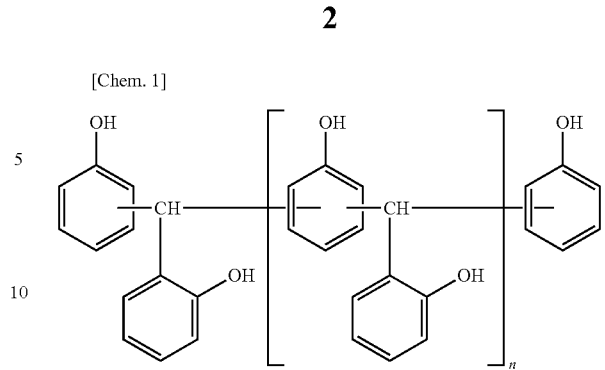

Such a compound containing a phenolic hydroxyl group exhibits excellent heat resistance in terms of the cured product; however, does not exhibit sufficient flame retardancy.

CITATION LIST

Patent Literature

[PTL 1] JP-A-2002-114889

SUMMARY OF INVENTION

Technical Problem

Therefore, an object of the present invention is to provide a compound containing a phenolic hydroxyl group, which exhibits excellent heat resistance and flame retardancy in terms of a cured product thereof, a phenolic resin including the same, a curable composition and a cured product thereof, a semiconductor sealing material, and a printed circuit board.

Solution to Problem

As a result of thorough studies in order to achieve the above object, the present inventors found that, since a reaction product of a compound having a quinone skeleton and phenol containing a hydrocarbon group or an alkoxy group has a molecular structure having a high hydroxyl group concentration, in which aromatic nuclei are mutually bonded not through a methylene chain, and the reactivity of the hydroxyl group is high, the reaction product exhibits excellent heat resistance and flame retardancy in terms of the cured product, and completed the present invention.

That is, the present invention relates to a compound containing a phenolic hydroxyl group, which has a molecular structure represented by the following General Formula (I):

[Chem. 2]

$$\text{OH} - \overset{}{\underset{}{X}} - \text{OH} \quad (I)$$

wherein X is a structural site represented by the following Structural Formula (x1) or (x2);

[Chem. 3]

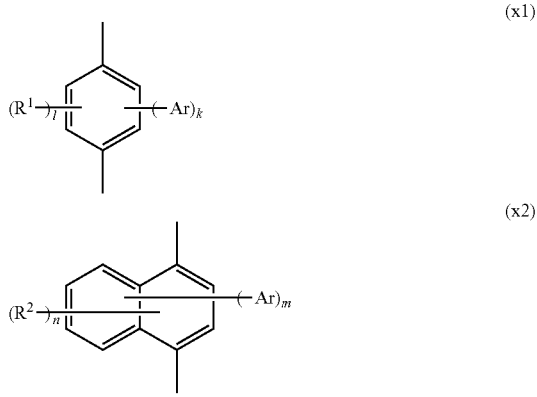

wherein, in Formula (x1) or (x2), each of $R^1$ and $R^2$ is any one of an alkyl group having 1 to 4 carbon atoms, an alkoxy group having 1 to 4 carbon atoms, an aryl group and an aralkyl group, l is an integer of 0 to 3, n is an integer of 0 to 4, in a case where l or n is 2 or greater, a plurality of $R^1$'s or $R^2$'s may be the same as or different from each other, k is an integer of 1 to 3, m is 1 or 2, and Ar is a structural site represented by the following Structural Formula (Ar1); and in a case where k or m is 2 or greater, a plurality of Ar's may be the same as or different from each other;

[Chem. 4]

wherein $R^3$ is any one of an alkyl group having 1 to 4 carbon atoms, an alkoxy group having 1 to 4 carbon atoms, an aryl group and an aralkyl group, q is an integer of 1 to 4, in a case where q is 2 or greater, a plurality of $R^3$'s may be the same as or different from each other, and p is 1 or 2.

The present invention further relates to a phenolic resin containing the compound containing a phenolic hydroxyl group.

The present invention still further relates to a preparation method of a phenolic resin, which includes reacting a compound (Q) having a quinone structure in the molecular structure and a compound (P) having a naphthol or dihydroxynaphthalene skeleton with each other.

The present invention still further relates to a phenolic resin prepared by the preparation method.

The present invention still further relates to a curable composition including the compound containing a phenolic hydroxyl group or the phenolic resin and a curing agent, as essential components.

The present invention still further relates to a cured product which is obtained by a curing reaction of the curable composition.

The present invention still further relates to a semiconductor sealing material containing the curable composition and an inorganic filler.

The present invention still further relates to a printed circuit board obtained by impregnating a reinforcement basic material with a resin composition varnished by blending the curable composition with an organic solvent, and superposing a copper foil on the resulting material, followed by heat-pressing.

Advantageous Effects of Invention

According to the present invention, it is possible to provide a compound containing a phenolic hydroxyl group, which has a low melt viscosity, and exhibits excellent heat resistance and flame retardancy in terms of the cured product, a phenolic resin including the same, a curable composition and a cured product thereof, a semiconductor sealing material, and a printed circuit board.

BRIEF DESCRIPTION OF DRAWINGS

FIG. 1 is a GPC chart of a phenolic resin (1) obtained in Example 1.
FIG. 2 is a 13C-NMR chart of the phenolic resin (1) obtained in Example 1.
FIG. 3 is an MS spectrum of the phenolic resin (1) obtained in Example 1.
FIG. 4 is a GPC chart of a phenolic resin (2) obtained in Example 2.
FIG. 5 is a GPC chart of a phenolic resin (3) obtained in Example 3.
FIG. 6 is an MS spectrum of the phenolic resin (3) obtained in Example 3.

DESCRIPTION OF EMBODIMENTS

Hereinafter, the present invention will be described in detail.

The compound containing a phenolic hydroxyl group of the present invention has a molecular structure represented by the following General Formula (I):

[Chem. 5]

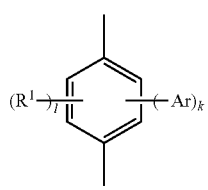

wherein X is a structural site represented by the following Structural Formula (x1) or (x2);

[Chem. 6]

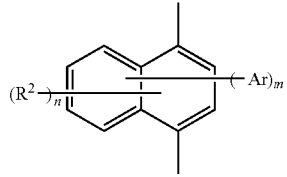

wherein, in Formula (x1) or (x2), each of $R^1$ and $R^2$ is any one of an alkyl group having 1 to 4 carbon atoms, an alkoxy group having 1 to 4 carbon atoms, an aryl group and an aralkyl group, l is an integer of 0 to 3, n is an integer of 0 to 4; in a case where l or n is 2 or greater, a plurality of $R^1$'s or $R^2$'s may be the same as or different from each other, k is an integer of 1 to 3, m is 1 or 2, Ar is a structural site represented by the following Structural Formula (Ar1), and in a case where k or m is 2 or greater, a plurality of Ar's may be the same as or different from each other;

[Chem. 7]

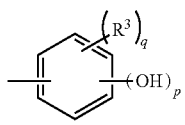

(Ar1)

wherein $R^3$ is any one of an alkyl group having 1 to 4 carbon atoms, an alkoxy group having 1 to 4 carbon atoms, an aryl group and an aralkyl group, q is an integer of 1 to 4, in a case where q is 2 or greater, a plurality of $R^3$'s may be the same as or different from each other, and p is 1 or 2.

The compound containing a phenolic hydroxyl group of the present invention represented by General Formula (I) has a low molecular weight, and a high aromatic ring concentration and a high hydroxyl group concentration since the compound containing a phenolic hydroxyl group has a structure in which aromatic nuclei are mutually bonded not through a methylene chain. Such a compound tends to be decreased in flame retardancy since, the concentration of a hydroxyl group having flammability is increased, and a large number of reactive groups exist in close proximity, while it exhibits excellent heat resistance in terms of a cured product thereof. In contrast, the compound containing a phenolic hydroxyl group of the present invention exhibits both excellent heat resistance and flame retardancy in terms of the cured product since the compound containing a phenolic hydroxyl group has a biphenyl skeleton or a terphenyl skeleton, and in Structural Formula (x1) or (x2) and two hydroxyl groups positioned at the para position of the aromatic nucleus have excellent reactivity.

As the compound represented by General Formula (I), a compound prepared by a method in which a compound (Q) having a quinone structure in the molecular structure and phenol (P) containing a hydrocarbon group or an alkoxy group are reacted with each other at a temperature range of 40° C. to 180° C. under non-catalytic or acid catalytic conditions is exemplified. In the case of preparing the compound containing a phenolic hydroxyl group of the present invention by such a method, it is possible to selectively prepare an arbitrary component according to the reaction conditions, or it is possible to prepare a phenolic resin which is a mixture of a plurality of compounds containing a phenolic hydroxyl group. In addition, only the arbitrary component may be isolated from the phenolic resin which is a mixture and used.

As the compound (Q) having a quinone structure in the molecular structure, the compound represented by the following Structural Formula (Q1) or (Q2) is exemplified:

[Chem. 8]

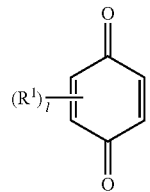

(Q1)

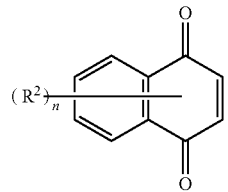

(Q2)

wherein, in Formula (Q1) or (Q2), each of $R^1$ and $R^2$ is any one of an alkyl group having 1 to 4 carbon atoms, an alkoxy group having 1 to 4 carbon atoms, an aryl group and an aralkyl group, l is an integer of 0 to 3, n is an integer of 0 to 4, and in a case where l or n is 2 or greater, a plurality of $R^1$'s or $R^2$'s may be the same as or different from each other.

Examples thereof include parabenzoquinone, 2-methyl benzoquinone, 2,3,5-trimethyl-benzoquinone, and naphthoquinone. These may be used alone respectively, or two or more kinds thereof may be used in combination.

As the phenol (P) containing a hydrocarbon group or an alkoxy group, the compound represented by the following Structural Formula (P1) is exemplified,

[Chem. 9]

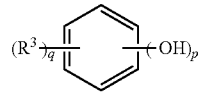

(P1)

in Formula (P1), $R^3$ is any one of an alkyl group having 1 to 4 carbon atoms, an alkoxy group having 1 to 4 carbon atoms, an aryl group and an aralkyl group, q is an integer of 1 to 4, in a case where q is 2 or greater, a plurality of $R^3$'s may be the same as or different from each other, and p is 1 or 2.

Examples thereof include ortho-cresol, meta-cresol, para-cresol, 2,6-dimethylphenol, 2,5-dimethylphenol, 2,4-dimethylphenol, 3,5-dimethylphenol, 2,3,4-trimethylphenol, 2,3,5-trimethylphenol, 2,3,6-trimethylphenol, 2,4,5-trimethylphenol, 3,4,5-trimethylphenol, 4-isopropylphenol, 4-tert-butylphenol, 2-methoxyphenol, 3-methoxyphenol, 4-methoxyphenol, 2-methoxy-4-methylphenol, 2-tert-butyl-4-methoxyphenol, 2,6-dimethoxyphenol, 3,5-dimethoxyphenol, 2-ethoxyphenol, 3-ethoxyphenol, 4-ethoxyphenol, 2-phenylphenol, 3-phenylphenol, 4-phenylphenol, and 4-benzylphenol are exemplified. These may be used alone respectively, or two or more kinds may be used in combination.

Among these, since heat resistance and flame retardancy of the cured product are excellent, a compound represented by General Formula (P1) in which $R^3$ is a methyl group is preferable, and cresol or dimethylphenol, which is a compound represented by General Formula (P1) in which the q value is 1 or 2 and the p value is 1, is more preferable.

Since the reactivity of the reaction of the compound (Q) having a quinone structure in the molecular structure with the phenol (P) containing a hydrocarbon group or an alkoxy group is high, the reaction proceeds even under non-catalytic conditions; however, the reaction may be performed by using a suitable acid catalyst. Examples of the acid catalyst used here include inorganic acids such as hydrochloric acid, sulfuric acid, and phosphoric acid, organic acids such as methanesulfonic acid, p-toluenesulfonic acid, and oxalic acid, or Lewis acids such as boron trifluoride, anhydrous aluminum chloride, and zinc chloride. In the case of using the acid catalyst described above, the acid catalyst is preferably used in the amount of 5.0% by mass or less with respect to the total mass of the compound (Q) having a quinone structure and the phenol (P) containing a hydrocarbon group or an alkoxy group.

In addition, the reaction is preferably performed under solvent-free conditions; however, the reaction may be performed in an organic solvent, as necessary. Examples of the organic solvent used here include methyl cellosolve, isopropyl alcohol, ethyl cellosolve, toluene, xylene, and methyl isobutyl ketone. In the case of using the organic solvent described above, the organic solvent is preferably used in a proportion within a range of 50 parts by mass to 200 parts by mass with respect to the total 100 parts by mass of the compound (Q) having a quinone structure and the phenol (P) containing a hydrocarbon group or an alkoxy group, from the viewpoint of improvement of reaction efficiency.

After the reaction of the compound (Q) having a quinone structure in the molecular structure with the phenol (P) containing a hydrocarbon group or an alkoxy group ends, drying under reduced pressure or the like is performed, whereby a desired compound containing a phenolic hydroxyl group or phenolic resin can be obtained.

The compound containing a phenolic hydroxyl group of the present invention exhibits the effects of the present invention in which heat resistance and flame retardancy of the cured product are excellent as long as the compound has the structure represented by General Formula (I). Hereinafter, more preferable compounds containing a phenolic hydroxyl group having the structure represented by General Formula (I) will be described in detail.

As a representative compound containing a phenolic hydroxyl group represented by the following General Formula (I), the compound containing a phenolic hydroxyl group represented by any one of the following Structural Formulas (I-1) to (I-3) is exemplified.

[Chem. 10]

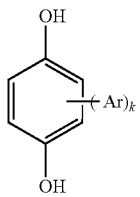

(I-1)

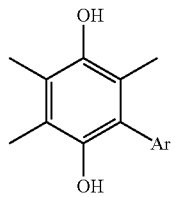

(I-2)

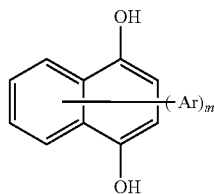

(I-3)

In Formulas (I-1) to (I-3), k is an integer of 1 to 3, m is 1 or 2, Ar is a structural site represented by the following Structural Formula (Ar1); and in a case where k or m is 2 or greater, a plurality of Ar's may be the same as or different from each other;

[Chem. 11]

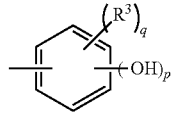

(Ar1)

in the formula, $R^3$ is any one of an alkyl group having 1 to 4 carbon atoms, an alkoxy group having 1 to 4 carbon atoms, an aryl group and an aralkyl group, q is an integer of 1 to 4, in a case where q is 2 or greater, a plurality of $R^3$'s may be the same as or different from each other, and p is 1 or 2.

As the compound containing a phenolic hydroxyl group represented by Structural Formula (I-1), more specifically, a compound represented by any one of the following Structural Formulas (1) to (3) is exemplified.

[Chem. 12]

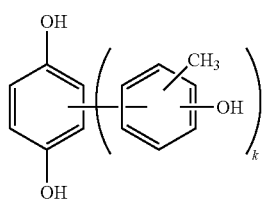

(1)

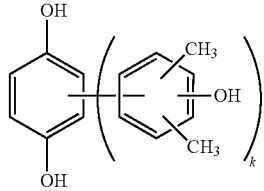

(2)

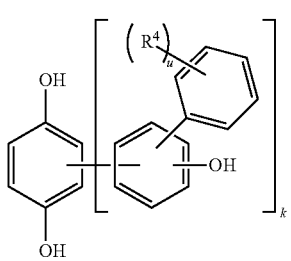

(3)

In Formulas (1) to (3), k is an integer of 1 to 3, $R^4$ is any one of an alkyl group having 1 to 4 carbon atoms, an alkoxy group having 1 to 4 carbon atoms, an aryl group and an aralkyl group, u is an integer of 1 to 4, and in a case where u is 2 or greater, a plurality of $R^4$'s may be the same as or different from each other.

Among the compounds containing a phenolic hydroxyl group of the present invention represented by General Formula (I), in particular, the compound containing a phenolic hydroxyl group represented by Structural Formula (1) exhibits excellent heat resistance and flame retardancy in terms of the cured product.

Among these, since heat resistance and flame retardancy of the cured product are particularly excellent, a phenolic resin containing a binuclear compound (x1) having the k value of 1 in Structural Formula (1) and a trinuclear compound (x2) having the k value of 2 in Structural Formula (1) is preferably used, and it is more preferable that the content of the binuclear compound (x1) in the phenolic resin is within a range of 2% to 50% in area ratio in a GPC measurement, and the content of the trinuclear compound (x2) is within a range of 10% to 95% in area ratio in a GPC measurement. Furthermore, it is particularly preferable that the content of the binuclear compound (x1) in the phenolic resin is within a range of 2% to 35% in area ratio in a GPC measurement, and the content of the trinuclear compound (x2) is within a range of 30% to 90% in area ratio in a GPC measurement.

Furthermore, from the viewpoint of obtaining a cured product having more excellent heat resistance, a phenolic resin containing a tetranuclear compound (x3) having the k value of 3 in Structural Formula (1) or the tetranuclear compound (x3') represented by the following Structural Formula (1'), in addition to the binuclear compound (x1) and the trinuclear compound (x2), is preferably used, and, at this time, the total content of the tetranuclear compound (x3) and the tetranuclear compound (x3') in the phenolic resin is preferably within a range of 2% to 20% in area ratio in a GPC measurement.

[Chem. 13]

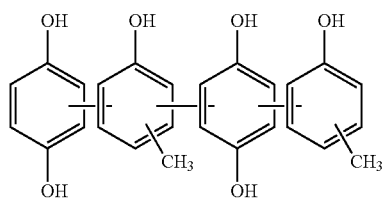

(1')

Moreover, in the present invention, the content of the binuclear compound (x1), the trinuclear compound (x2), the tetranuclear compound (x3), the tetranuclear compound (x3'), and other components in a phenolic resin refers to a proportion of the peak area of each component with respect to the total peak area of the phenolic resin, which is calculated from GPC measurement data under the following conditions.

<GPC Measurement Conditions>
Measurement apparatus: "HLC-8220 GPC" manufactured by Tosoh Corporation
Column: guard column "HXL-L" manufactured by Tosoh Corporation
+"TSK-GEL G2000HXL" manufactured by Tosoh Corporation
+"TSK-GEL G2000HXL" manufactured by Tosoh Corporation
+"TSK-GEL G3000HXL" manufactured by Tosoh Corporation
+"TSK-GEL G4000HXL" manufactured by Tosoh Corporation
Detector: RI (differential refractometer)
Data processing: "GPC-8020 model II Version 4.10" manufactured by Tosoh Corporation
Measurement Conditions:

| | |
|---|---|
| column temperature | 40° C. |
| eluent | tetrahydrofuran |
| flow rate | 1.0 ml/min |

Standard: according to the measurement manual of the "GPC-8020 model II Version 4.10", the following monodisperse polystyrene of which the molecular weight is known is used.
(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Sample: a solution (50 μl) obtained by filtering a tetrahydrofuran solution of 1.0% by mass in terms of the resin solid content through a microfilter.

The compound represented by Structural Formula (1) can be prepared by the method described above, for example, using parabenzoquinone as the compound (Q) having a quinone structure in the molecular structure and cresol as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between parabenzoquinone and cresol is preferably a proportion in which naphtol is within a range of 0.1 moles to 10.0 moles with respect to 1 mole of parabenzoquinone.

The cresol used here may be any one of ortho-cresol, meta-cresol, and para-cresol, and plural types thereof may be used in combination. Among these, ortho-cresol is preferable since a phenolic resin which has low melt viscosity and exhibits excellent heat resistance and flame retardancy in terms of the cured product is obtained.

As the compound represented by Structural Formula (1), a compound represented by any one of the following Structural Formulas (1-1) to (1-31) is exemplified.
[Chem. 14]
(1-1)
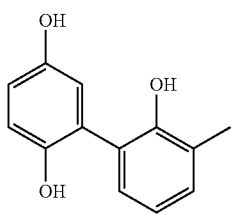
(1-2)
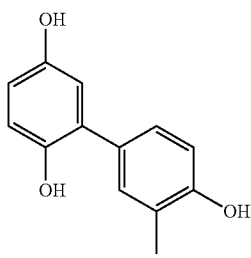
(1-3)
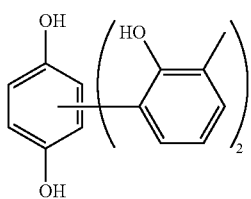
(1-4)
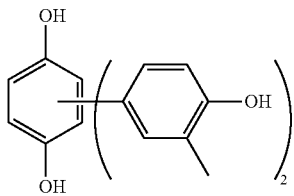
(1-5)
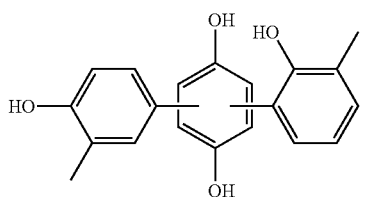
(1-6)
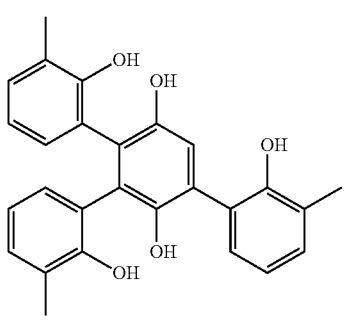
(1-7)
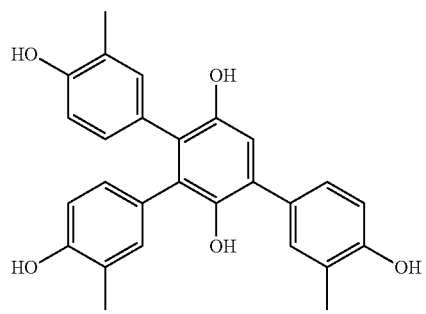
(1-8)
(1-9)
[Chem. 15]
(1-10)
(1-11)
(1-12)
(1-13)

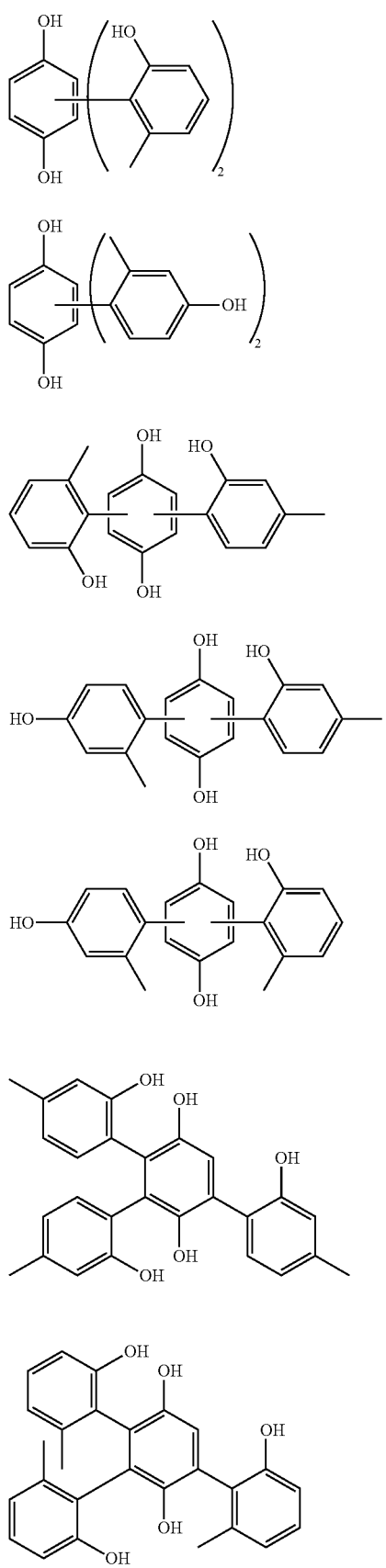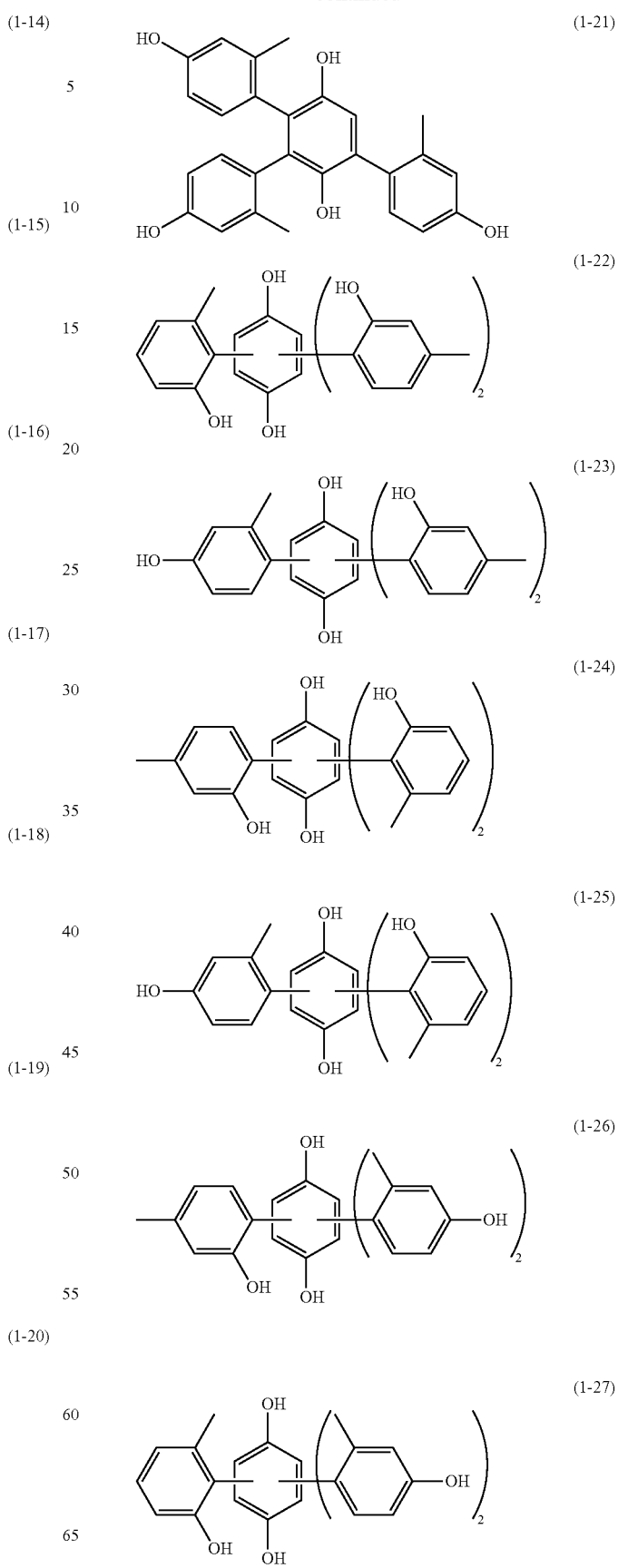

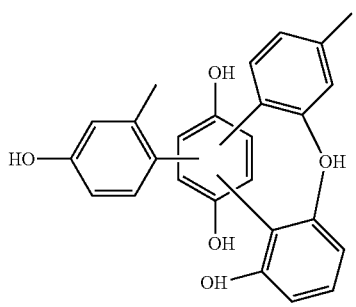
(1-28)

[Chem. 16]

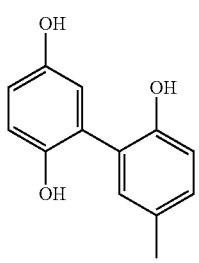
(1-29)

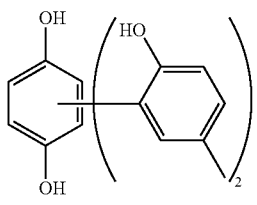
(1-30)

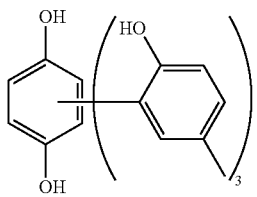
(1-31)

Among the compounds containing a phenolic hydroxyl group of the present invention represented by General Formula (I), in particular, the compound containing a phenolic hydroxyl group represented by Structural Formula (2) exhibits excellent heat resistance and flame retardancy in terms of the cured product.

Among these, since heat resistance and flame retardancy of the cured product are more excellent, a phenolic resin containing the binuclear compound (x1) having the k value of 1 in Structural Formula (2) and the trinuclear compound (x2) having the k value of 2 in Structural Formula (2) is preferably used, and it is more preferable that the content of the binuclear compound (x1) in the phenolic resin is within a range of 2% to 50% in area ratio in a GPC measurement, and the content of the trinuclear compound (x2) is within a range of 10% to 95% in area ratio in a GPC measurement. Furthermore, it is particularly preferable that the content of the binuclear compound (x1) in the epoxy resin is within a range of 2% to 35% in area ratio in a GPC measurement, and the content of the trinuclear compound (x2) is within a range of 30% to 95% in area ratio in a GPC measurement.

Furthermore, from the viewpoint of obtaining a cured product having more excellent heat resistance, a phenolic resin containing the tetranuclear compound (x3) having the k value of 3 in Structural Formula (2) or the tetranuclear compound (x3') represented by the following Structural Formula (2'), in addition to the binuclear compound (x1) and the trinuclear compound (x2), is preferably used, and, at this time, the total content of the tetranuclear compound (x3) and the tetranuclear compound (x3') in the phenolic resin is preferably within a range of 2% to 20% in area ratio in a GPC measurement.

[Chem. 17]

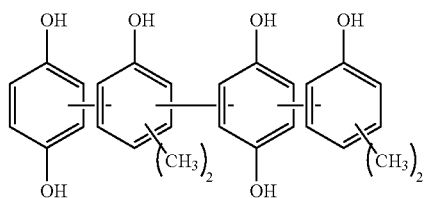
(2')

The compound containing a phenolic hydroxyl group represented by Structural Formula (2) can be prepared by the method described above, for example, using parabenzoquinone as the compound (Q) having a quinone structure in the molecular structure and dimethylphenol as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between parabenzoquinone and dimethylphenol is preferably a proportion in which dimethylphenol is within a range of 0.1 moles to 10.0 moles with respect to 1 mole of parabenzoquinone.

The dimethylphenol used here may be any regioisomer of 2,6-dimethylphenol, 2,5-dimethylphenol, 2,4-dimethylphenol, and 3,5-dimethylphenol. Among these, 2,6-dimethylphenol is preferable since a phenolic resin which has low melt viscosity and exhibits excellent heat resistance and flame retardancy in terms of the cured product is obtained.

As the compound represented by Structural Formula (2), a compound represented by any one of the following Structural Formulas (2-1) to (2-3) is exemplified.

[Chem. 18]

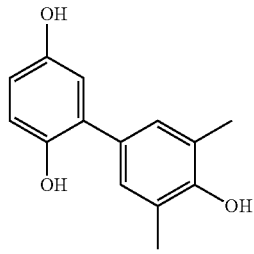
(2-1)

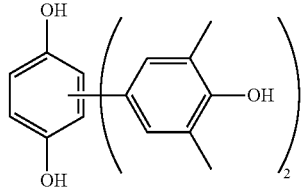
(2-2)

-continued (2-3)
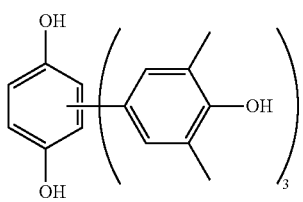

The compound containing a phenolic hydroxyl group represented by Structural Formula (3) can be prepared by the method described above, for example, using parabenzoquinone as the compound (Q) having a quinone structure in the molecular structure and a phenylphenol compound as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between parabenzoquinone and the phenylphenol compound is preferably a proportion in which the phenylphenol compound is within a range of 0.1 moles to 10.0 moles with respect to 1 mole of parabenzoquinone.

As the compound represented by Structural Formula (3), a compound represented by any one of the following Structural Formulas (3-1) to (3-12) is exemplified.

[Chem. 19]

(3-1)
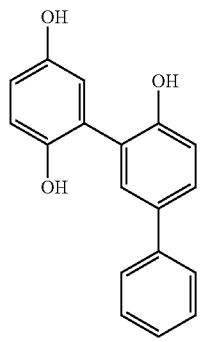

(3-2)
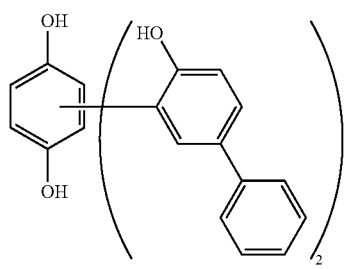

(3-3)
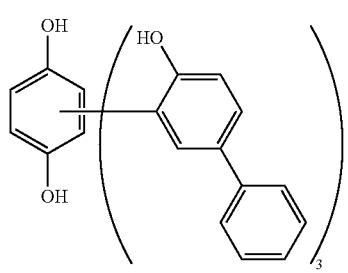

-continued (3-4)
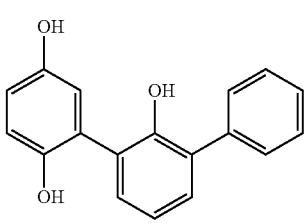

(3-5)
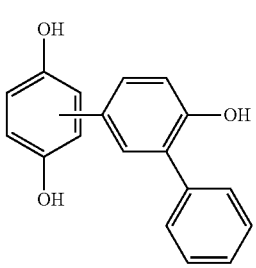

(3-6)
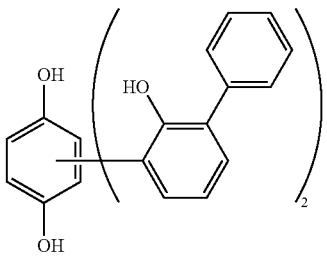

(3-7)
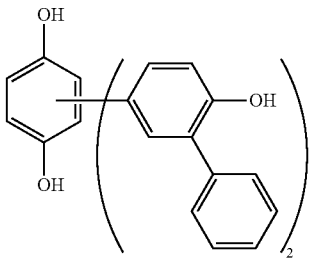

(3-8)
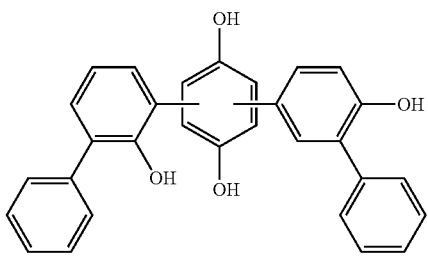

(3-9)
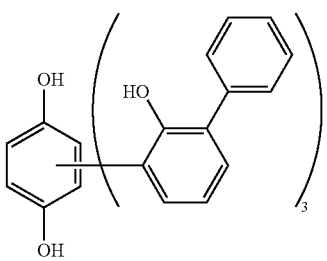

-continued

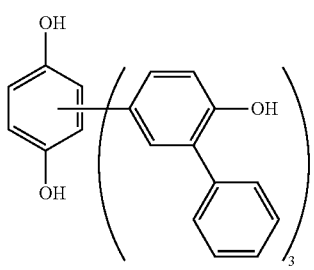
(3-10)

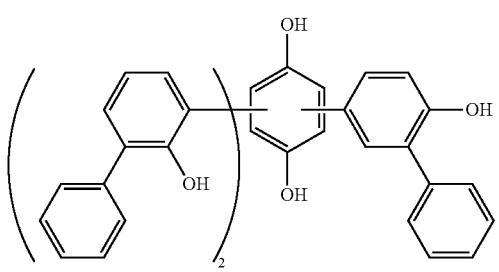
(3-11)

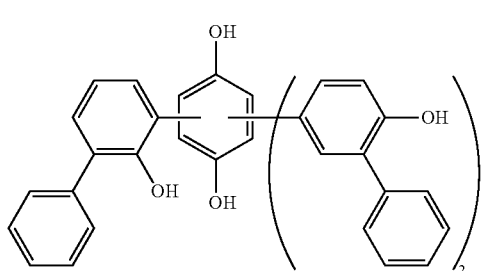
(3-12)

As the compound containing a phenolic hydroxyl group represented by Structural Formula (1-2), more specifically, a compound represented by any one of the following Structural Formulas (4) and (5) is exemplified.

[Chem. 20]

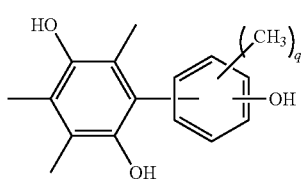
(4)

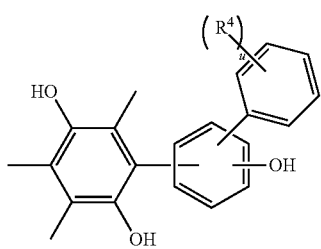
(5)

In Formula (4), q is 1 or 2, in Formula (5), $R^4$ is any one of an alkyl group having 1 to 4 carbon atoms, an alkoxy group having 1 to 4 carbon atoms, an aryl group and an aralkyl group, u is an integer of 1 to 4, and in a case where u is 2 or greater, a plurality of $R^4$'s may be the same as or different from each other.

The compound containing a phenolic hydroxyl group represented by Structural Formula (4) can be prepared by the method described above, for example, using 2,3,5-trimethyl-parabenzoquinone as the compound (Q) having a quinone structure in the molecular structure and cresol or dimethyl-phenol as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between 2,3,5-trimethyl-parabenzoquinone and cresol or dimethylphenol is preferably a proportion in which cresol or dimethylphenol is within a range of 0.1 moles to 10.0 moles with respect to 1 mole of 2,3,5-trimethyl-parabenzoquinone.

As the compound represented by Structural Formula (4), a compound represented by any one of the following Structural Formulas (4-1) to (4-7) is exemplified.

[Chem. 21]

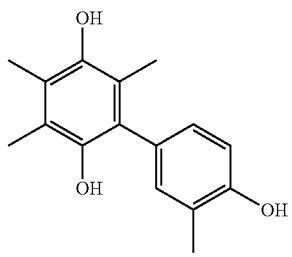
(4-1)

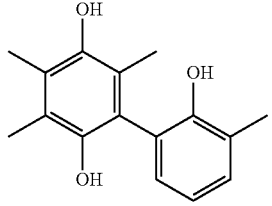
(4-2)

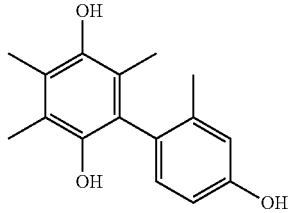
(4-3)

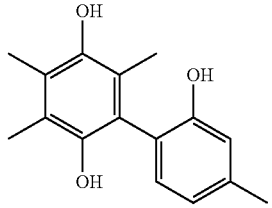
(4-4)

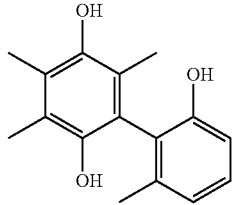
(4-5)

-continued (4-6)

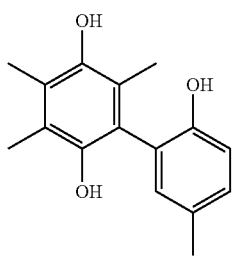

(4-7)

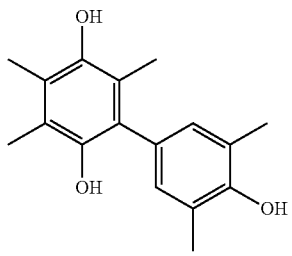

The compound containing a phenolic hydroxyl group represented by Structural Formula (5) can be prepared by the method described above, for example, using 2,3,5-trimethyl-parabenzoquinone as the compound (Q) having a quinone structure in the molecular structure and a phenylphenol compound as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between 2,3,5-trimethyl-parabenzoquinone and a phenylphenol compound is preferably a proportion in which the phenylphenol compound is within a range of 0.1 moles to 10.0 moles with respect to 1 mole of 2,3,5-trimethyl-parabenzoquinone.

As the compound represented by Structural Formula (5), a compound represented by any one of the following Structural Formulas (5-1) to (5-3) is exemplified.

[Chem. 22]

(5-1)

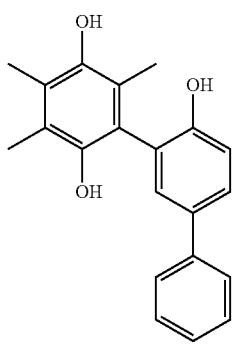

(5-2)

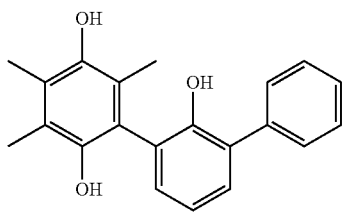

(5-3)

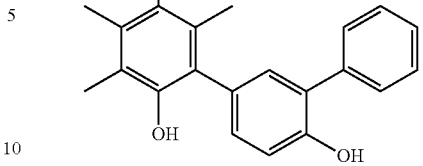

As the compound containing a phenolic hydroxyl group represented by Structural Formula (1-3), more specifically, the compound containing a phenolic hydroxyl group represented by any one of the following Structural Formulas (6) and (7) is exemplified.

[Chem. 23]

(6)

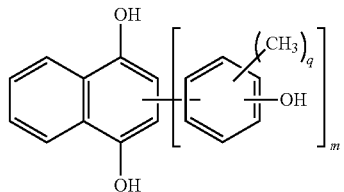

(7)

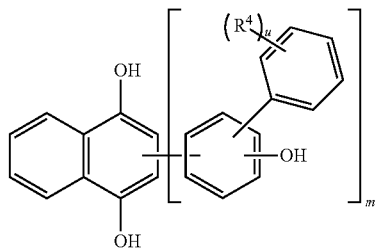

In the formula, each of m and q is 1 or 2, $R^4$ is any one of an alkyl group having 1 to 4 carbon atoms, an alkoxy group having 1 to 4 carbon atoms, an aryl group and an aralkyl group, u is an integer of 1 to 4, and in a case where u is 2 or greater, a plurality of $R^4$'s may be the same as or different from each other.

The compound containing a phenolic hydroxyl group represented by Structural Formula (6) can be prepared by the method described above, for example, using naphthoquinone as the compound (Q) having a quinone structure in the molecular structure and cresol or dimethylphenol as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between naphthoquinone and cresol or dimethylphenol is preferably a proportion in which the cresol or dimethylphenol is within a range of 0.1 moles to 10.0 moles with respect to 1 mole of naphthoquinone.

As the compound represented by Structural Formula (6), a compound represented by any one of the following Structural Formulas (6-1) to (6-7) is exemplified.

[Chem. 24]

(6-1) 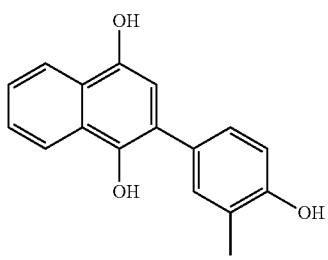

(6-2) 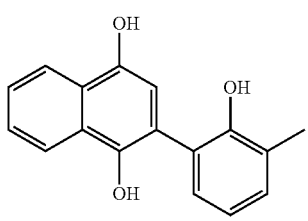

(6-3) 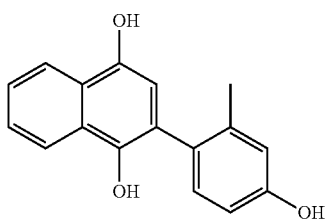

(6-4) 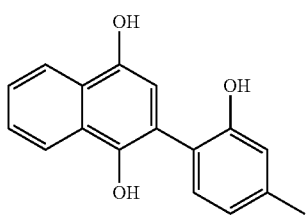

(6-5) 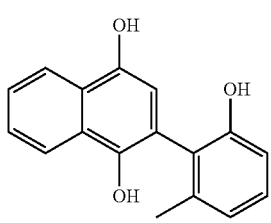

(6-6) 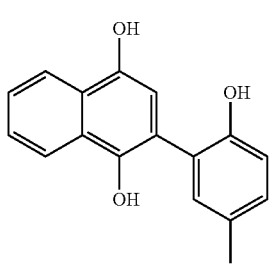

(6-7) 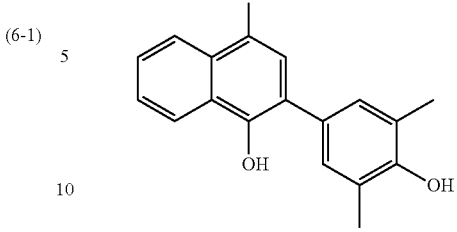

The compound containing a phenolic hydroxyl group represented by Structural Formula (7) can be prepared by the method described above, for example, using naphthoquinone as the compound (Q) having a quinone structure in the molecular structure and a phenylphenol compound as the phenol (P) containing a hydrocarbon group or an alkoxy group. At this time, since a phenolic resin which has low melt viscosity and exhibits more excellent heat resistance and flame retardancy in terms of the cured product is obtained, the reaction proportion between naphthoquinone and the phenylphenol compound is preferably a proportion in which the phenylphenol compound is within a range of 0.1 moles to 10.0 moles with respect to 1 mole of naphthoquinone.

As the compound represented by Structural Formula (7), a compound represented by any one of the following Structural Formulas (7-1) to (7-7) is exemplified.

[Chem. 25]

(7-1) 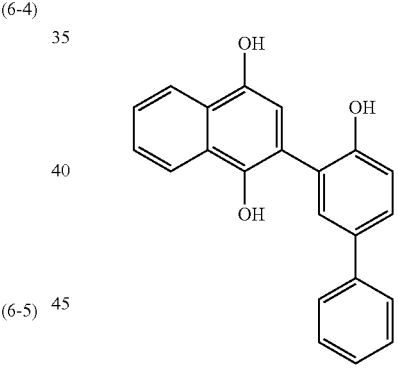

(7-2) 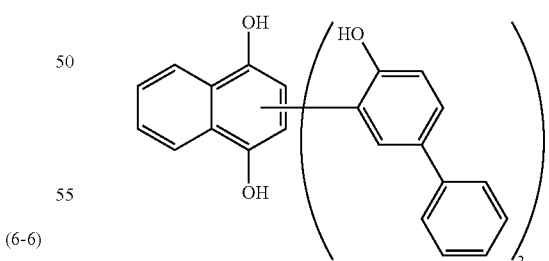

(7-3) 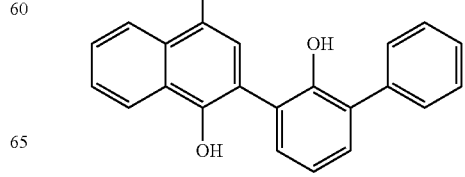

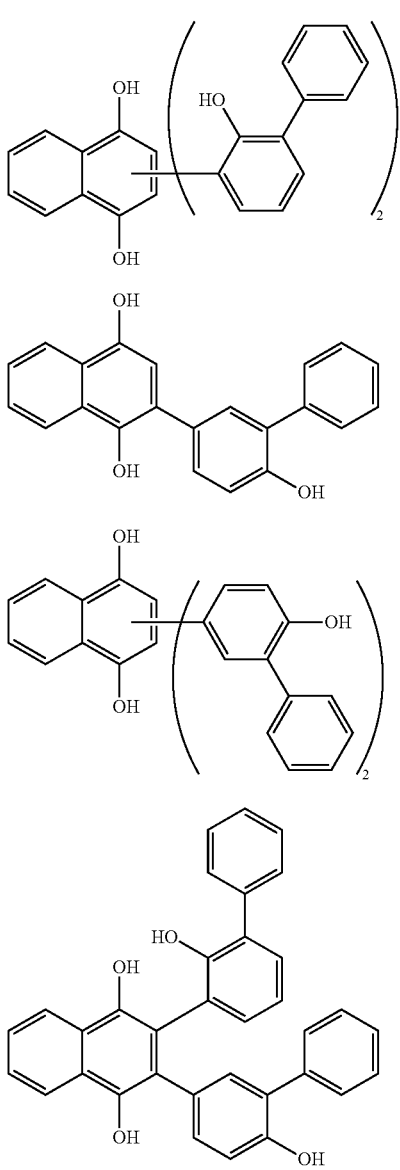

(7-4)

(7-5)

(7-6)

(7-7)

Among the compounds containing a phenolic hydroxyl group exemplified above, the compound containing a phenolic hydroxyl group represented by Structural Formula (1) or (2) is preferable from the viewpoint of excellent balance between heat resistance and flame retardancy of the cured product.

In a phenolic resin including the compound containing a phenolic hydroxyl group of the present invention, the hydroxyl equivalent is preferably within a range of 70 g/eq to 150 g/eq from the viewpoint of excellent curing properties.

The curable composition of the present invention contains the compound containing a phenolic hydroxyl group described above or a phenolic resin including the same, and a curing agent as essential components. As the curing agent, an epoxy resin is exemplified.

Specific examples of the epoxy resin used here include naphthalene skeleton-containing epoxy resins such as 1,6-diglycidyloxy naphthalene, 2,7-diglycidyloxy naphthalene, an α-naphthol novolak type epoxy resin, a β-naphthol novolak type epoxy resin, polyglycidyl ether of α-naphthol/β-naphthol co-condensed novolak, a naphthol aralkyl type epoxy resin, and 1,1-bis(2,7-diglycidyloxy-1-naphthyl)alkane; bisphenol type epoxy resins such as a bisphenol A type epoxy resin and a bisphenol F type epoxy resin; biphenyl type epoxy resins such as a biphenyl type epoxy resin and a tetramethyl biphenyl type epoxy resin; novolak type epoxy resins such as a phenol novolak type epoxy resin, a cresol novolak type epoxy resin, a bisphenol A novolak type epoxy resin, a bisphenol F novolak type epoxy resin, an epoxidized product of a condensate of a phenol-based compound and an aromatic aldehyde having a phenolic hydroxyl group, and a biphenyl novolak type epoxy resin; triphenylmethane type epoxy resins; tetraphenyl ethane type epoxy resins; dicyclopentadiene-phenol addition reaction type epoxy resins; phenol aralkyl type epoxy resins; phosphorus atom-containing epoxy resins; and modified epoxy resins of the present invention.

In the case of using an epoxy resin as a curing agent, the blending proportion between the compound containing a phenolic hydroxyl group or the phenolic resin and the epoxy resin is preferably a proportion in which the equivalent ratio (phenolic hydroxyl group/epoxy group) of the phenolic hydroxyl group in the compound containing a phenolic hydroxyl group or the phenolic resin to the epoxy group in the epoxy resin is 1/0.5 to 1/1.5 since reactivity and heat resistance in terms of a cured product thereof are excellent at this proportion.

In addition, in the case of using an epoxy resin as a curing agent, in addition to the compound containing a phenolic hydroxyl group or the phenolic resin of the present invention, other curing agents for epoxy resin may be used in combination. As other curing agents for epoxy resin, various known curing agents such as an amine-based compound, an amide-based compound, an acid anhydride-based compound, and a phenol-based compound are exemplified. Specifically, examples of the amine-based compound include diaminodiphenyl methane, diethylenetriamine, triethylenetetramine, diaminodiphenyl sulfone, isophoronediamine, imidazole, BF₃-amine complex, and guanidine derivatives, examples of the amide-based compound include dicyandiamide and a polyamide resin synthesized from a linolenic acid dimer and ethylenediamine, examples of the acid anhydride-based compound include phthalic anhydride, trimellitic anhydride, pyromellitic anhydride, maleic anhydride, tetrahydrophthalic anhydride, methyl tetrahydrophthalic anhydride, methylnadic anhydride, hexahydrophthalic anhydride, and methylhexahydrophthalic anhydride, and examples of the phenol-based compound include polyvalent phenolic compounds such as a phenol novolak resin, a cresol novolak resin, an aromatic hydrocarbon formaldehyde resin-modified phenolic resin, a dicyclopentadiene phenol adduct type resin, a phenol aralkyl resin (Xylok resin), a naphthol aralkyl resin, a triphenylol methane resin, a tetraphenylol ethane resin, a naphthol novolak resin, a naphthol-phenol co-condensed novolak resin, a naphthol-cresol co-condensed novolak resin, a biphenyl-modified phenolic resin (polyvalent phenolic compound in which a phenolic nucleus is linked by a bismethylene group), a biphenyl-modified naphthol resin (polyvalent naphthol compound in which a phenolic nucleus is linked by a bismethylene group), an aminotriazine-modified phenolic resin (polyvalent phenolic compound in which a phenolic nucleus is linked by melamine, benzoguanamine, or the like), and an alkoxy group-containing aromatic ring-modified novolak resin (polyvalent phenolic compound in which a phenolic nucleus and an alkoxy group-containing aromatic ring are linked by a formaldehyde).

In the case of using other curing agents for epoxy resin, the blending proportion between the compound containing a phenolic hydroxyl group or the phenolic resin of the present invention and other curing agents for epoxy resin is not particularly limited as long as the characteristics of the compound containing a phenolic hydroxyl group of the application which exhibits excellent heat resistance and flame retardancy in terms of a cured product thereof are not impaired, and, for example, the compound containing a phenolic hydroxyl group or the phenolic resin of the present invention is preferably within a range of 5 parts by mass to 95 parts by mass in 100 parts by mass of the total mass of both.

In addition, in the case of using other curing agents for epoxy resin, the blending proportion with the epoxy resin is preferably a proportion in which the equivalent ratio (active hydrogen atom/epoxy group) between the total of active hydrogen atoms contained in the compound containing a phenolic hydroxyl group or the phenolic resin of the present invention and other curing agent for epoxy resin, and the epoxy group contained in the epoxy resin is 1/0.5 to 1/1.5 since reactivity and heat resistance of the cured product are excellent at this proportion.

In the curable composition of the present invention, a curing promoter can also be suitably used in combination as necessary. As the curing promoter, various curing promoters can be used, and examples thereof include phosphorus-based compounds, tertiary amines, imidazoles, organic acid metal salts, Lewis acids, and amine complex salts. In particular, in the case of using the curing promoter as semiconductor sealing material applications, 2-ethyl-4-methylimidazole as the imidazole compounds, triphenylphosphine as the phosphorus-based compounds, and 1,8-diazabicyclo-[5.4.0]-undecene (DBU) as the tertiary amines are preferable from the viewpoint of excellent curing properties, heat resistance, electrical characteristics, and moisture resistance reliability.

The curable composition of the present invention described above may further contain other additive components depending on the applications or the desired performance. Specifically, for the purposes of further improving flame retardancy, a non-halogen-based flame retardant which substantially does not contain a halogen atom may be blended.

Examples of the non-halogen-based flame retardant include a phosphorus-based flame retardant, a nitrogen-based flame retardant, a silicone-based flame retardant, an inorganic flame retardant, and an organometallic salt-based flame retardant. These may be used alone respectively, or plural types thereof may be used in combination.

As the phosphorus-based flame retardant, any of an inorganic flame retardant and an organic flame retardant can be used. Examples of the inorganic compound include red phosphorus and an inorganic nitrogene-containing phosphorus compound such as ammonium phosphates, e.g., monoammonium phosphate, diammonium phosphate, triammonium phosphate or ammonium polyphosphate; and amide phosphate.

The red phosphorus is preferably subjected to a surface treatment for the purpose of preventing hydrolysis or the like, and examples of the surface treatment method include (i) a method for coat-treating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a method for coat-treating with an inorganic compound such as magnesium hydroxide, aluminum hydroxide, zinc hydroxide, or titanium hydroxide, and a mixture of a thermosetting resin such as a phenolic resin, and (iii) a method for doubly coat-treating the surface of a coated film of an inorganic compound such as magnesium hydroxide, aluminum hydroxide, zinc hydroxide, or titanium hydroxide with a thermosetting resin such as a phenolic resin.

Examples of the organic phosphorus-based compound include general-purpose organic phosphorus-based compounds such as a phosphoric acid ester compound, a phosphonic acid compound, a phosphinic acid compound, a phosphine oxide compound, a phosphorane compound, and an organic nitrogen-containing phosphorus compound, and cyclic organic phosphorus compounds such as 9,10-dihydro-9-oxa-10-phosphaphenanthrene-10-oxide, 10-(2,5-dihydroxyphenyl)-10H-9-oxa-10-phosphaphenanthrene-10-oxide, and 10-(2,7-dihydroxynaphthyl)-10H-9-oxa-10-phosphaphenanthrene-10-oxide, and derivatives obtained by reacting this with a compound such as an epoxy resin or a phenolic resin.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition obtained by blending all of a compound containing a phenolic hydroxyl group or a phenolic resin, a curing agent, and other additives, or a filler.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition.

In addition, in the case of using the phosphorus-based flame retardant, the phosphorus-based flame retardant may be used in combination with hydrotalcite, magnesium hydroxide, a boron compound, zirconium oxide, black dye, calcium carbonate, zeolite, zinc molybdate, or activated charcoal.

Examples of the nitrogen-based flame retardant include a triazine compound, a cyanuric acid compound, an isocyanuric acid compound, and phenothiazine, and the triazine compound, the cyanuric acid compound, or the isocyanuric acid compound is preferable.

Examples of the triazine compound include (i) aminotriazine sulfate compounds such as guanylic melamine sulfate, melem sulfate, and melam sulfate, (ii) co-condensates of a phenol-base compound such as phenol, cresol, xylenol, butylphenol, or nonylphenol, and melamines such as melamine, benzoguanamine, acetoguanamine, or formguanamine and formaldehyde, (iii) a mixture of the co-condensates of (ii) and phenolic resins such as a phenolformaldehyde condensate or the like, (iv) a product obtained by further modifying (ii) and (iii) with tung oil or isomerized linseed oil, or the like, in addition to melamine, acetoguanamine, benzoguanamine, melon, melam, succinoguanamine, ethylene dimelamine, melamine polyphosphate, and triguanamine.

Examples of the cyanuric acid compound can include cyanuric acid and melamine cyanurate.

The blending amount of the nitrogen-based flame retardant is suitably selected depending on the type of the nitrogen-based flame retardant, other components of a curable composition, and the desired degree of flame retardancy, and for example, the nitrogen-based flame retardant is preferably blended within a range of 0.05 parts by mass to 10 parts by mass, and particularly preferably blended within a range of 0.1 parts by mass to 5 parts by mass, in 100 parts by mass of the curable composition.

In addition, when using the nitrogen-based flame retardant, metal hydroxide or a molybdenum compound may be used in combination.

The silicone-based flame retardant can be used without any particular limitation as long as the silicone-based flame retardant is an organic compound containing a silicon atom, and examples thereof include silicone oil, silicone rubber, and silicone resins.

The blending amount of the silicone-based flame retardant is suitably selected depending on the type of the silicone-based flame retardant, other components of a curable composition, and the desired degree of flame retardancy, and for example, the silicone-based flame retardant is preferably blended within a range of 0.05 parts by mass to 20 parts by mass in 100 parts by mass of the curable composition. In addition, when using the silicone-based flame retardant, a molybdenum compound or alumina may be used in combination.

Examples of the inorganic flame retardant include metal hydroxides, metal oxides, metal carbonate compounds, metal powder, boron compounds, and low melting point glass.

Examples of the metal hydroxide can include aluminum hydroxide, magnesium hydroxide, dolomite, hydrotalcite, calcium hydroxide, barium hydroxide, and zirconium hydroxide.

Examples of the metal oxide can include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Examples of the metal carbonate compound can include zinc carbonate, magnesium carbonate, calcium carbonate, barium carbonate, basic magnesium carbonate, aluminum carbonate, iron carbonate, cobalt carbonate, and titanium carbonate.

Examples of the metal powder can include aluminum powder, iron powder, titanium powder, manganese powder, zinc powder, molybdenum powder, cobalt powder, bismuth powder, chromium powder, nickel powder, copper powder, tungsten powder, and tin powder.

Examples of the boron compound can include zinc borate, zinc metaborate, barium metaborate, boric acid, and borax.

Examples of the low melting point glass can include glass-like compounds such as a Ceepree (Bokusui Brown Co., Ltd.) glass, a hydrated glass $SiO_2$—$MgO$—$H_2O$, $PbO$—$B_2O_3$-based glass, a $ZnO$—$P_2O_5$—$MgO$-based glass, a $P_2O_5$—$B_2O_3$—$PbO$—$MgO$-based glass, a P—Sn—O—F-based glass, a $PbO$—$V_2O_5$—$TeO_2$-based glass, an $Al_2O_3$—$H_2O$-based glass, and lead borosilicate-based glass.

The blending amount of the inorganic flame retardant is suitably selected depending on the type of the inorganic flame retardant, other components of a curable composition, and the desired degree of flame retardancy, and for example, the inorganic flame retardant is preferably blended within a range of 0.5 parts by mass to 50 parts by mass, and particularly preferably blended within a range of 5 parts by mass to 30 parts by mass in 100 parts by mass of the curable composition.

Examples of the organometallic salt-based flame retardant include ferrocene, an acetylacetonate metal complex, an organometallic carbonyl compound, an organic cobalt salt compound, an organic sulfonic acid metal salt, and a compound obtained by an ionic bond or a coordination bond of a metal atom to an aromatic compound or a heterocyclic compound.

The blending amount of the organometallic salt-based flame retardant is suitably selected depending on the type of the organometallic salt-based flame retardant, other components of a curable composition, and the desired degree of flame retardancy, and for example, the organometallic salt-based flame retardant is preferably blended within a range of 0.005 parts by mass to 10 parts by mass in 100 parts by mass of the curable composition.

In addition, various compounding agents such as a silane coupling agent, a release agent, a pigment, and an emulsifier can be added to the curable composition of the present invention, as necessary.

In the curable composition of the present invention, an inorganic filler can be blended, as necessary. The compound containing a phenolic hydroxyl group and the phenolic resin used in the present invention can be suitably used, in particular, in semiconductor sealing material applications.

Examples of the inorganic filler include fused silica, crystalline silica, alumina, silicon nitride, and aluminum hydroxide. Among these, the fused silica is preferable since greater amount of the inorganic filler can be blended. The fused silica can be used in any one of a crushed shape or a spherical shape; however, in order to increase the blending amount of the fused silica and to suppress increase in melt viscosity of the curable composition, spherical silica is preferably mainly used. Furthermore, in order to increase the blending amount of the spherical silica, the particle size distribution of the spherical silica is preferably suitably adjusted. The filling ratio is preferably within a range of 0.5 parts by mass to 95 parts by mass in 100 parts by mass of the curable composition.

In addition, in the case of using the curable composition of the present invention in applications such as a conductive paste, it is possible to use a conductive filler such as silver powder or copper powder.

In the case of preparing the curable composition of the present invention in a varnish for a printed circuit board, an organic solvent is preferably blended. Examples of the organic solvent capable of being used here include methyl ethyl ketone, acetone, dimethylformamide, methyl isobutyl ketone, methoxypropanol, cyclohexanone, methyl cellosolve, ethyl diglycol acetate, and propylene glycol monomethyl ether acetate, and the selection and the suitable amount to be used can be suitably selected depending on the application, and, for example, in printed circuit board applications, polar solvents such as methyl ethyl ketone, acetone, and dimethylformamide having the boiling point of 160° C. or lower are preferable, and the solvents are preferably used in a proportion in which the non-volatile content becomes 40% by mass to 80% by mass. On the other hand, in adhesive film applications for build-up, as the organic solvent, for example, ketones such as acetone, methyl ethyl ketone, and cyclohexanone, acetic acid esters such as ethyl acetate, butyl acetate, cellosolve acetate, propylene glycol monomethyl ether acetate, and carbitol acetate, carbitols such as cellosolve and butyl carbitol, aromatic hydrocarbons such as toluene and xylene, dimethylformamide, dimethylacetamide, or N-methylpyrrolidone are preferably used, and the solvents are preferably used in a proportion in which the non-volatile content becomes 30% by mass to 60% by mass.

The curable composition of the present invention is obtained by uniformly mixing the respective components described above. The curable composition of the present invention obtained by blending a compound containing a phenolic hydroxyl group or a resin, a curing agent, and as necessary, a curing promoter can be easily cured by the same methods as methods known in the related art, whereby a cured product is formed. Examples of the cured product include molded cured products such as a laminate, a cast material, an adhesive layer, a coating film, and a film.

The compound containing a phenolic hydroxyl group and the phenolic resin of the present invention can be used in various electronic material applications since the melt viscosity is low, and heat resistance and flame retardancy of the cured product are excellent. Among these, by taking advantage of low melt viscosity thereof, the compound containing a phenolic hydroxyl group and the phenolic resin can be suitably used, in particular, in semiconductor sealing material applications.

The semiconductor sealing material can be prepared by a method in which a mixture of a phenol component including the compound containing a phenolic hydroxyl group or the phenolic resin of the present invention, a curing agent, and a filler is sufficiently mixed until it becomes uniform using an extruder, a kneader, or a roll. As the filler used here, the inorganic fillers described above are exemplified, and, as described above, the filler is preferably used within a range of 0.5 parts by mass to 95 parts by mass in 100 parts by mass of the curable composition. Among these, the filler is preferably used within a range of 70 parts by mass to 95 parts by mass, and particularly preferably used within a range of 80 parts by mass to 95 parts by mass, since flame retardancy, moisture resistance, and soldering crack resistance are improved, and a linear expansion coefficient can be reduced.

As a method for molding a semiconductor package using the obtained semiconductor sealing material, a method in which the semiconductor sealing material is formed using a casting, a transfer forming machine, or an injection molding machine, and the resultant product is heated for 2 hours to 10 hours under temperature conditions of 50° C. to 200° C. is exemplified, and by such a method, it is possible to obtain a semiconductor device which is a molded product.

In addition, in production of a printed circuit board using the compound containing a phenolic hydroxyl group or the phenolic resin of the present invention, a method which includes impregnating a reinforcement basic material with a varnish-like curable composition including the compound containing a phenolic hydroxyl group or the phenolic resin of the present invention, a curing agent, an organic solvent, and other additives, and superposing a copper foil on the resulting material, followed by heat-pressing is exemplified. Examples of the reinforcement basic material capable of being used here include paper, glass cloth, glass nonwoven fabric, aramid paper, aramid cloth, glass mat, and glass roving cloth. In describing the method in more detail, first, the varnish-like curable composition described above is heated at a heating temperature according to the solvent species used, preferably 50° C. to 170° C., whereby prepreg is obtained which is a cured product. The mass proportion between the curable composition and the reinforcement basic material used at this time is not particularly limited; however, typically, the prepreg is preferably prepared such that the resin content in the prepreg is 20% by mass to 60% by mass. Next, the prepreg obtained in the above manner is laminated by an ordinary method, then, copper foil is suitably superposed thereon, and the resultant product is heat-pressed at 170° C. to 250° C. for 10 minutes to 3 hours under a pressure of 1 MPa to 10 MPa, whereby a desired printed circuit board is obtained.

EXAMPLES

Hereinafter, the present invention will be more specifically described using examples and comparative examples, and "parts" and "%" below are based on mass unless otherwise specifically indicated. Moreover, GPC, NMR, an MS spectrum were measured under the following conditions.

GPC: the measurement conditions are as follows.
Measurement apparatus: "HLC-8220 GPC" manufactured by Tosoh Corporation
Column: guard column "HXL-L" manufactured by Tosoh Corporation
+"TSK-GEL G2000HXL" manufactured by Tosoh Corporation
+"TSK-GEL G2000HXL" manufactured by Tosoh Corporation
+"TSK-GEL G3000HXL" manufactured by Tosoh Corporation
+"TSK-GEL G4000HXL" manufactured by Tosoh Corporation
Detector: RI (differential refractometer)
Data processing: "GPC-8020 model II Version 4.10" manufactured by Tosoh Corporation
Measurement conditions: column temperature 40° C.
eluent: tetrahydrofuran
flow rate 1.0 ml/min
Standard: according to the measurement manual the "GPC-8020 model II Version 4.10", the following monodisperse polystyrene of which the molecular weight is known is used.
(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Sample: a solution (50 μl) obtained by filtering a tetrahydrofuran solution of 1.0% by mass in terms of the resin solid content through a microfilter.
$^{13}$C-NMR: the measurement conditions are as follows.
Apparatus: AL-400 manufactured by JEOL Ltd.
Measurement mode: SGNNE (1H complete decoupling method of NOE elimination)
Solvent: dimethylsulfoxide Pulse angle: 45° pulse Sample concentration: 30% by weight Cumulated number: 10,000 times MS: double focusing mass spectrometer "AX505H (FD505H)" manufactured by JEOL Ltd.

EXAMPLE 1

Preparation of Phenolic Resin (1)

649 parts by mass (6.0 moles) of ortho-cresol, 162 parts by mass (1.5 moles) of parabenzoquinone, 8 parts by mass of para-toluenesulfonic acid were put into a flask equipped with a thermometer, a dropping funnel, a cooling tube, a fractionating column and a stirrer, and the resultant product was heated from room temperature to 120° C. with stirring. After the temperature reached 120° C., stirring was performed for 2 hours. After the reaction ended, the precipitated crystal product was filtered, and washed with 200 parts by mass of water two times. Thereafter, the resultant product was dried under heating under reduced pressure, whereby 117 parts by mass of a phenolic resin (1) was obtained. A GPC chart of the obtained phenolic resin (1) is shown in FIG. 1, a 13C-NMR spectrum of the obtained phenolic resin (1) is shown in FIG. 2, and an MS spectrum of the obtained phenolic resin (1) is shown in FIG. 3. The hydroxyl equivalent of the phenolic resin (1) was 81 g/eq, and a peak of 216 corresponding to the binuclear compound (x1) represented by the following Structural Formula (a-1), a peak of 322 corresponding to the trinuclear compound (x2) represented by the following Structural Formula (b-1), and a peak of 428 corresponding to the tetranuclear compound (x3) represented by the following Structural Formula (c-1) were detected from the MS spectrum. The content of the component corresponding to the binuclear compound (x1) was 4.6%, the content of the component corresponding to the trinuclear compound (x2) was 88.0%, and the content of the component corresponding to the tetranuclear compound (x3) was 5.1% in the phenolic resin, calculated from the GPC chart.

[Chem. 26]

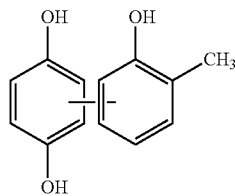
(a-1)

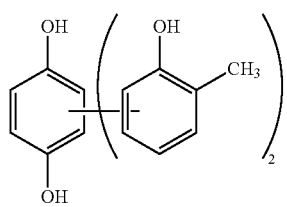
(b-2)

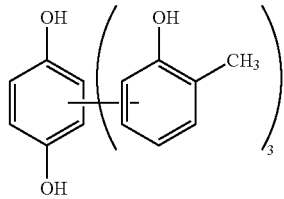
(c-3)

EXAMPLE 2

Preparation of Phenolic Resin (2)

649 parts by mass (6.0 moles) of ortho-cresol and 3 parts by mass of para-toluenesulfonic acid were put into a flask equipped with a thermometer, a dropping funnel, a cooling tube, a fractionating column, and a stirrer, and the resultant product was heated from room temperature to 80° C. with stirring. After the temperature reached 80° C., 162 parts by mass (1.5 moles) of parabenzoquinone was added thereto over 1 hour, then, the temperature was raised to 130° C., and stirring was performed for 1 hour for reaction. After the reaction ended, the resultant product was dried under reduced pressure, whereby 260 parts by mass of a phenolic resin (2) was obtained. A GPC chart of the obtained phenolic resin (2) is shown in FIG. 4. The hydroxyl equivalent of the phenolic resin (2) was 97 g/eq. The content of the component corresponding to the binuclear compound (x1) was 25.8%, the content of the component corresponding to the trinuclear compound (x2) was 51.7%, and the content of the component corresponding to the tetranuclear compound (x3) was 10.0% in the phenolic resin, calculated from the GPC chart.

EXAMPLE 3

Preparation of Phenolic Resin (3)

733 parts by mass (6.0 moles) of 2,6-dimethylphenol, 216 parts by mass (2.0 moles) of parabenzoquinone, 9 parts by mass of para-toluenesulfonic acid were put into a flask equipped with a thermometer, a dropping funnel, a cooling tube, a fractionating column and a stirrer, and the resultant product was heated from room temperature to 120° C. with stirring. After the temperature reached 120° C., stirring was performed for 2 hours. After the reaction ended, the precipitated crystal product was filtered, and washed with 200 parts by mass of water two times. Thereafter, the resultant product was dried under heating under reduced pressure, whereby 123 parts by mass of a phenolic resin (3) was obtained. A GPC chart of the obtained phenolic resin (3) is shown in FIG. 5, and an MS spectrum of the obtained phenolic resin (3) is shown in FIG. 6. The hydroxyl equivalent of the phenolic resin (3) was 88 g/eq, and a peak of 230 corresponding to the compound represented by the following Structural Formula (a-2), a peak of 350 corresponding to the compound represented by the following Structural Formula (b-2), and a peak of 470 corresponding to the compound represented by the following Structural Formula (c-2) were detected from the MS spectrum. The content of the component corresponding to the binuclear compound (x1) was 8.0%, the content of the component corresponding to the trinuclear compound (x2) was 87.8%, and the content of the component corresponding to the tetranuclear compound (x3) was 1.6% in the phenolic resin, calculated from the GPC chart.

[Chem. 27]

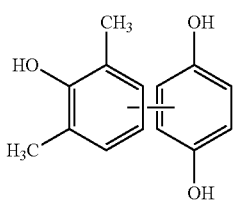
(a-2)

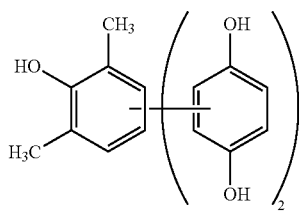
(b-2)

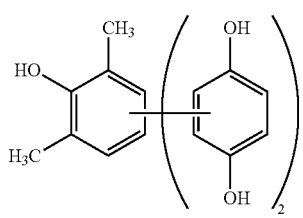
(c-2)

EXAMPLES 4 TO 6 AND COMPARATIVE EXAMPLE 1

Evaluation test of heat resistance and flame retardancy was performed on the phenolic resins (1) to (3) obtained above, and a phenolic resin (1') for comparison [triphenylmethane type phenolic resin ("MEH-7500" manufactured by Meiwa Plastic Industries, Ltd., hydroxyl equivalent of 98 g/eq)] in the following manner.

<Evaluation of Heat Resistance>

1) Production of Evaluation Sample

Any one of the phenolic resins (1) to (3), and (1'), a naphthalene type epoxy resin ("EXA-4750" manufactured by DIC Corporation, epoxy equivalent of 188 g/eq) as a curing agent, and triphenylphosphine (hereinafter, abbreviated as "TPP") as a curing promoter were blended according to the composition ratios shown in the following Table 2, whereby curable compositions were obtained. Each of these was poured into a mold of 11 cm×9 cm×2.4 mm and molded at a temperature of 150° C. for 10 minutes using a press. After the molded product was taken out from the mold, the molded product was postcured at a temperature of 175° C. for 5 hours, whereby an evaluation sample was obtained.

2) Measurement of Glass Transition Temperature

A measurement of the temperature at which the change in elastic modulus becomes maximum (at which tan δ change ratio is the greatest) was performed on the evaluation sample using a viscoelasticity measuring apparatus (DMA: solid viscoelasticity measuring apparatus RSAII manufactured by Rheometric Scientific Inc., rectangular tension method; frequency of 1 Hz, temperature raising rate of 3° C./min), and this is evaluated as the glass transition temperature. The results are shown in Table 1.

TABLE 1

Table 1

| | Example 4 | Example 5 | Example 6 | Comparative Example 1 |
|---|---|---|---|---|
| Phenolic resin (1) | 30.1 | | | |
| Phenolic resin (2) | | 34.0 | | |
| Phenolic resin (3) | | | 31.9 | |
| MEH-7500 | | | | 34.3 |
| EXA-4750 | 69.9 | 66.0 | 68.1 | 65.7 |
| TPP | 1.0 | 1.0 | 1.0 | 1.0 |
| Heat resistance (° C.) | 234 | 230 | 225 | 215 |

<Evaluation of Flame Retardancy>

1) Production of Evaluation Sample

Any one of the phenolic resins (1), (2), and (1'), a naphthalene type epoxy resin ("EXA-4750" manufactured by DIC Corporation, epoxy equivalent of 188 g/eq) as a curing agent, triphenylphosphine (hereinafter, abbreviated as "TPP") as a curing promoter, spherical silica ("FB-5604" manufactured by Denki Kagaku Kogyo Kabushiki Kaisha) as an inorganic filler, a coupling agent ("KBM-403" manufactured by Shin-Etsu Chemical Co., Ltd.) as a silane coupling agent, carnauba wax ("PEARL WAX No. 1-P" manufactured by Cerarica Noda Co., Ltd.), and carbon black were blended according to the composition ratios shown in the following Table 3, and the resultant products were melted and kneaded at a temperature of 85° C. for 5 minutes using a two roll, whereby curable compositions were obtained. Using the obtained curable composition, a sample having a size of 12.7 mm in width, 127 mm in length and 1.6 mm in thickness was molded at a temperature of 175° C. for 90 seconds using a transfer molding machine, and the sample was postcured at a temperature of 175° C. for 5 hours, whereby an evaluation sample was obtained.

2) Evaluation of Flame Retardancy

A combustion test was performed on the five samples for evaluation having a thickness of 1.6 mm obtained in the above according to the UL-94 test method. The results are shown in Table 2.

Flame Retardant Test Class

*1: maximum combustion time (seconds) in a single flame contact

*2: total combustion time (seconds) of five test pieces

TABLE 2

Table 2

| | Example 4 | Example 5 | Example 6 | Comparative Example 1 |
|---|---|---|---|---|
| Phenolic resin (1) | 35.5 | | | |
| Phenolic resin (2) | | 40.2 | | |
| Phenolic resin (3) | | | 37.6 | |
| MEH-7500 | | | | 40.4 |
| EXA-4750 | 82.5 | 77.8 | 80.4 | 77.6 |
| TPP | 2 | 2 | 2 | 2 |
| Spherical silica | 870 | 870 | 870 | 870 |
| Coupling agent | 4 | 4 | 4 | 4 |
| Carnauba wax | 4 | 4 | 4 | 4 |
| Carbon black | 2 | 2 | 2 | 2 |
| Flame retardant test class | V-0 | V-0 | V-0 | Combustion |
| *1 | 6 | 8 | 6 | 38 |
| *2 | 42 | 47 | 39 | 266 |

The invention claimed is:

1. A compound containing a phenolic hydroxyl group, which has a molecular structure represented by the following General Formula (I):

[Chem. 1]

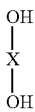

OH
|
X
|
OH
(I)

wherein X is a structural site represented by the following Structural Formula (x2);

[Chem. 2]

[Chem. 2]

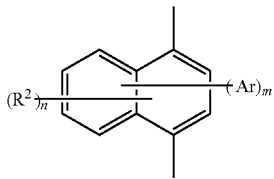

(x2)

wherein, in Formula (x2), $R^2$ is any one of an alkyl group having 1 to 4 carbon atoms, an alkoxy group having 1 to 4 carbon atoms, an aryl group and an aralkyl group, n is an integer of 0 to 4, in a case where n is 2 or greater, a plurality of $R^2$'s may be the same as or different from each other, m is 1 or 2, Ar is a structural site represented by the following Structural Formula (Ar1), and in a case where m is 2 or greater, a plurality of Ar's may be the same as or different from each other;

[Chem. 3]

(Ar1)

wherein $R^3$ is any one of an alkyl group having 1 to 4 carbon atoms, an alkoxy group having 1 to 4 carbon atoms, an aryl group and an aralkyl group, q is an integer of 1 to 4, in a case where q is 2 or greater, a plurality of $R^3$'s may be the same as or different from each other and p is 1 or 2.

2. A curable composition, comprising as essential components:
the compound containing a phenolic hydroxyl group according to claim 1; and
a curing agent.

3. A cured product which is obtained by a curing reaction of the curable composition according to claim 2.

4. A semiconductor sealing material, comprising:
the curable composition according to claim 2; and
an inorganic filler.

5. A printed circuit board obtained by impregnating a reinforcement basic material with a resin composition varnished by blending the curable composition according to claim 2 with an organic solvent, and superposing a copper foil on the resulting material, followed by heat-pressing.

* * * * *